United States Patent
Hirota et al.

(10) Patent No.: US 7,351,866 B2
(45) Date of Patent: Apr. 1, 2008

(54) METHOD FOR MANUFACTURING TERTIARY AMINE

(75) Inventors: Atsushi Hirota, Wakayama (JP); Toru Nishimura, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/668,172

(22) Filed: Jan. 29, 2007

(65) Prior Publication Data

US 2007/0179320 A1 Aug. 2, 2007

(30) Foreign Application Priority Data

Jan. 30, 2006 (JP) .............................. 2006-020210

(51) Int. Cl.
   *C07C 209/16* (2006.01)
   *C07C 209/60* (2006.01)
(52) U.S. Cl. ...................................... 564/479; 564/480
(58) Field of Classification Search ................ None
   See application file for complete search history.

(56) References Cited

U.S. PATENT DOCUMENTS 6,632,414 B2 * 10/2003 Liu ............................ 423/659

FOREIGN PATENT DOCUMENTS

| JO | 2004-526032 | 8/2004 |
| JP | 6-211754 | 8/1994 |
| JP | 2003-176255 | 6/2003 |

OTHER PUBLICATIONS

Database CAPLUS on STN, Acc. No. 2003:801525, Kolev et al., Chemical Engineering and Processing (2004), 43(1), p. 1-7 (abstract).*

Said Irandoust, et al. "Competitive Hydrodesulfurization and Hydrogenation in a Monolithic Reactor", Aiche Journal, vol. 36, No. 5, May 1990, pp. 746-752.

Vasillos Hatziantoniou, et al. "The Segmented Two Phase Flow Monolithic Catalyst Reactor. An Alternative for Liquid-Phase Hydrogenations", Ind. Eng. Chem. Fundam., vol. 23, 1984, pp. 82-88.

* cited by examiner

*Primary Examiner*—Brian Davis
(74) *Attorney, Agent, or Firm*—Oblon, Spivak, McClelland, Maier & Neustadt, P.C.

(57) ABSTRACT

The invention provides a method for manufacturing a tertiary amine, including reacting a tertiary amine with an alcohol and a primary or secondary amine in a reactor loaded with a film type catalyst, controlling the superficial velocity of liquid in the reactor at 0.1 cm/s or more.

5 Claims, 1 Drawing Sheet

METHOD FOR MANUFACTURING TERTIARY AMINE

FIELD OF THE INVENTION

The present invention relates to a method for manufacturing a tertiary amine corresponding to an alcohol and a primary or secondary amine as raw materials, using a film type catalyst.

BACKGROUND OF THE INVENTION

Many of industrial reactions are carried out in a mixing tank type reactor using solid catalyst slurry and contacting liquid with a reactive gas, such as hydrogen or ammonia, in the presence of the catalyst to allow them to react. After the end of the reaction, generally, the catalyst is removed with filtration to collect the reaction product.

However, a slurried catalyst has problems in safety, increase in waste material, operability and productivity. For example, there are such problems that many of catalysts are spontaneously combustible and powder and slurry catalysts must be handled with care, and that the catalyst must be removed by filtration etc. in order to collect the reaction product thereby leading to complex facilities and operation.

As a process that requires neither a mixing operation by stirring or gas bubbling nor filtration separation of a catalyst, there can be mentioned a fixed-bed system. As to forms of a catalyst for use in the fixed-bed system, a molded catalyst of a pellet shape, noodle shape, or tablet shape has been well known conventionally. By subjecting powdery material having a catalyst activity to molding processing by such method as compression or extrusion into the above-mentioned form, a construction having an infinite number of fine pores therein is formed to satisfy both of the catalyst configuration and great surface area. For example, it is disclosed in JP-A 6-211754.

According to the reaction system, such problem as handleability of the catalyst and waste material can be solved, but there are many reactions to which the system can not be applied. For example, there were such instances that temperature control was troublesome in reactions accompanied with absorption or generation of heat, and that uneven liquid-gas distribution in a reactor sometimes resulted in an insufficient reaction percentage or many side reactions caused by local concentration gradient.

In tertiary amination reaction, when trying to obtain reaction product at a high reaction percentage using the molded catalyst described in JP-A 6-211754, no small amount of undesirable side products are generated. As the side product, in addition to wax or an aldol condensate generated caused by a side reaction of alcohol as the raw material, there can be mentioned ammonia generated due to disproportionation of primary or secondary amine and tertiary amine as side product from primary or secondary amine. Various improvements have been carried out for practicing the technique highly selectively while suppressing these side products.

In JP-A 2003-176255 a reactor in which a catalyst metal is adhered on the surface of monolith is disclosed. In the reactor, such advantage is noted that, in a hydrogenation reaction between a gas and liquid, material transfer is accelerated compared with a fixed-bed packed reactor of a conventional type, because the pressure drop of the reactor is small and the velocity of the gas and liquid can be made large. However, although a reaction of a compound containing a nitrogen atom is intended, only such instance is expressed clearly as a reaction according to a simple mechanism such as hydrogenation. Examples disclosed in addition to this aims to limited applications such as, mainly, hydrogenation reaction.

JP-A 2004-526032 discloses a gas-liquid reaction method having a process of running and transferring a gas-liquid feed flow in a monolithic structure catalyst bed, wherein the liquid in the feed fluid is run and transferred through the reaction path at a running liquid superficial velocity in a range of 0.01-10 cm/s, and the gas is run and transferred at a gas:liquid volume ratio G:L in a range of gas of 1-4000 gas standard state liter/liquid liter. In the document, there is described that, compared with various research results reported in conventional documents in which a reactor is operated, generally, at a comparatively high liquid superficial velocity (e.g., 30 cm/s) and a comparatively small gas/liquid ratio (e.g., 0.5 V/V) in order to maintain so-called Taylor flow conditions in a honeycomb passage, the method can easily achieve one pass inversion percentage of more than 50% on an industrial scale whether or not the Taylor flow is maintained. However, the conditions in the case where a reaction system is not specified is only means for trying to gain staying time in a catalyst bed for the purpose of attaining a design suitable for use in a single-pass reactor system. In AIChE Journal, 36, 746 (1990) cited in JP-A 2004-526032, there is already disclosed such experimental conditions as, in hydrogenation reaction of thiophene/cyclohexane with a CoMo/alumina monolithic catalyst, a liquid superficial velocity of 3.5 cm/s or less (the average of gas-liquid superficial velocity is 3.5 cm/s or less) and a gas-liquid ratio of 15 standard state litter/liquid litter or more (a gas feed rate of 3 standard state litter/h or more, a liquid feed rate of 200 mL/h or less). Further, in Ind. Eng. Chem. Fundam., 23, 82 (1984) such experimental conditions are adopted as a liquid superficial velocity of around 1.2 cm/s and gas/liquid ratio of around 3 V/V in hydrogenation reaction of nitrobenzoic acid with a monolithic palladium catalyst.

SUMMARY OF THE INVENTION

The invention provides a method for manufacturing a tertiary amine, including reacting a tertiary amine with an alcohol and a primary or secondary amine in a reactor loaded with a film type catalyst, controlling the superficial velocity of liquid in the reactor at 0.1 cm/s or more.

DETAILED DESCRIPTION OF THE INVENTION

Figure 1:
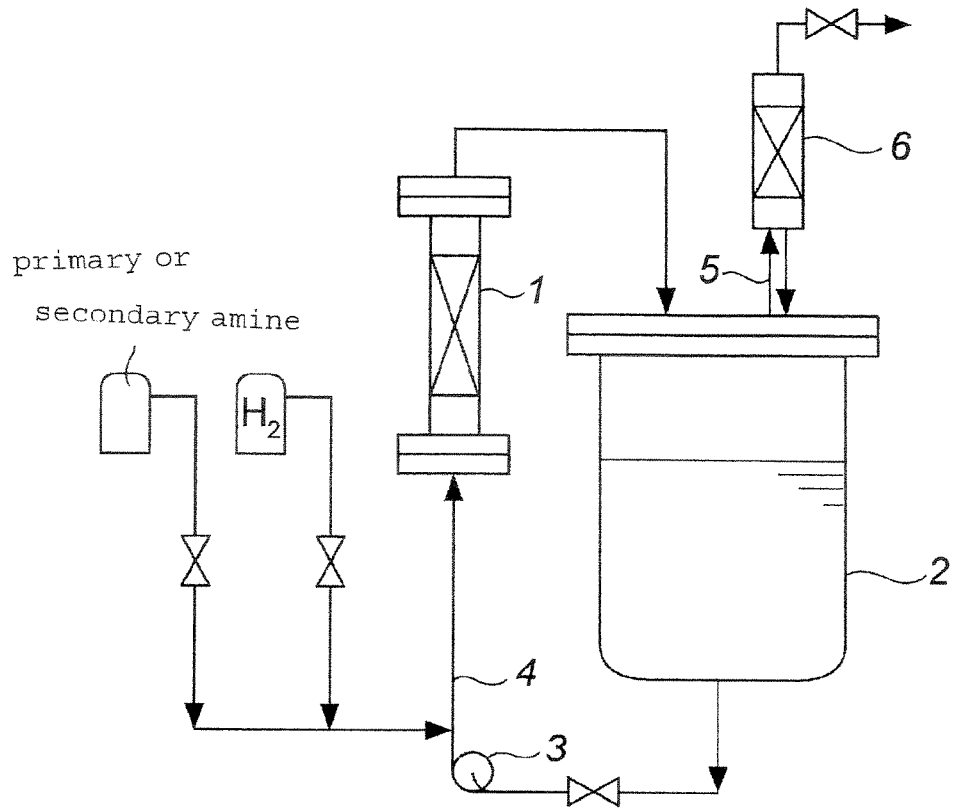
FIG. 1 shows a summary drawing showing one example of the circulation fixed-bed type reaction apparatus for use in the present invention.

In JP-A 6-211754, it is difficult up to now to practice the reaction highly selectively by a simple process.

In JP-A 2003-176255, there has never been an example in which it is applied to such reaction having extremely complex mechanism that alcohol and primary or secondary amine are used as raw materials to manufacture corresponding tertiary amine to improve the yield.

Thus, except when a reaction system is specified, it has not been known up to now to foresee an advantageous reaction condition by limiting liquid superficial velocity alone.

The present invention relates to a method for manufacturing an intended tertiary amine at a high yield, manufacturing a tertiary amine from the reaction of an alcohol and a primary or secondary amine with a film type catalyst.

According to the method of the present invention, an intended tertiary amine can be obtained at a high yield with a simple process that does not require any separation operation of the catalyst.

Examples of the alcohol as a raw material for use in the method for manufacturing a tertiary amine of the present invention include linear or branched, saturated or unsaturated aliphatic alcohols having 8-36 carbon atoms. Specifically, such alcohols can be exemplified as octyl alcohol, lauryl alcohol, myristyl alcohol, stearyl alcohol, behenyl alcohol, oleyl alcohol, mixed alcohols thereof, Ziegler alcohol obtained by the Ziegler method, and an oxo alcohol and a Guelbet alcohol obtained by the oxo method.

Examples of the primary or secondary amine as a raw material for use in the manufacturing method of tertiary amine of the present invention include aliphatic primary or secondary amines, including methylamine, dimethylamine, ethylamine, diethylamine, dodecylamine or didodecylamine.

The tertiary amine obtained from corresponding alcohol and primary or secondary amine as raw materials is an amine in which a hydrogen atom bonding to the nitrogen atom of the primary or secondary amine is substituted by an alkyl and/or alkenyl group derived from the alcohol. For example, the corresponding tertiary amine obtained from lauryl alcohol and dimethylamine is N-dodecyl-N,N-dimethylamine, which is distinguished from tertiary amines, that is, N,N-didodecyl-N-methylamine and N,N,N-tridodecylamine being side products of the reaction between methylamine generated by disproportionation of dimethylamine and ammonia.

The film type catalyst for use in the present invention indicates a catalyst having a thin film-like form with a thickness of 500 μm or less, differing from conventional ones of irregularly packed type having a size of around several millimeters. The migrating process of reacting substances and reaction product within the catalyst body is of diffusion control, and, by shortening the distance down to 500 μm or less, it is possible to accelerate material transfer between the inside and outside of the catalyst body to allow even the inside of the catalyst body to be utilized effectively, and, at the same time, to suppress hyperreaction of intermediate reaction substances in the inside of the catalyst body. In particular, the thickness is preferably 100 μm or less because the reaction activity per the catalyst mass is significantly enhanced, and 50 μm or less is more preferred. The lower limit of the thickness is preferably 0.01 μm, more preferably 1 μm for the purpose of securing the strength and obtaining the durability in the strength of the catalyst layer.

The film type catalyst can have various configurations as the structure in accordance with the form of a reactor. For example, there can be mentioned such catalysts as a catalyst coating layer formed on the inside wall surface of a tube, and a catalyst molded in thin plates that divide the inside of a tube into plural flow passes in the axial direction. It is preferred to have a construction that allows the feed of reacting substances to the catalyst body and the collection of the reaction product from the catalyst body to occur easily. In addition, for the purpose of allowing the reaction to proceed effectively, it is preferred to arrange the catalyst body surface, onto which the reacting substances are fed and from which a reaction product is collected, as wide as possible. In order to satisfy the prerequisite, suitably used are an aggregate formed by bundling tubes having an inner diameter of several millimeters to a few dozen millimeters, and a structure formed by arranging a film type catalyst on the inner surface of a honeycomb structure having a cell density of a few dozen cells to a few hundred cells per square inches, etc.

In order to give above-mentioned various structures to the film type catalyst, for example, there is such method as molding a catalytically active material itself to make it into a honeycomb-like structure, but from a viewpoint of satisfying both of a thin catalyst layer and a high mechanical strength, it is preferred to fix a film type catalyst on the surface of a support Preferably the support is made of metal foil. For example, as described above, there can be mentioned a method in which a coating layer including a catalytically active material is formed on the surface of a rigid support such as metal having a tube-like, flat plate-like or honeycomb-like shape to form a film type catalyst. As the coating method at this time, conventionally publicly known methods can be used, including, for example, a physical evaporation method such as sputtering, chemical evaporation method, impregnation method from a solution system and, in addition, various types of coating method such as blade, spray, dip, spin, gravure and die coatings using a binder.

There is no particular limitation on an active material that constitutes the film type catalyst and publicly known ones can be utilized. Generally, copper-based metals etc. can be preferably used, and ones containing copper are more preferred. For example, there can be mentioned copper alone, and ones containing two metal components formed by adding copper with a transition metal element such as Cr, Co, Ni, Fe or Mn, wherein one containing Cu and Ni is used preferably. Further, ones containing three or more metal components are used preferably. Ones in which the above-mentioned material is further carried on a carrier such as silica, alumina, titania or zeolite are also used.

There may be incorporated in the inside of the film type catalyst with a binder that does not act individually as an active material and fixes an active material to form a film type catalyst body. As the binder, a polymer or inorganic compound, that gives adhesiveness between active materials or an active material and the support surface, and that has such properties, in addition, as chemical resistance and heat resistance capable of bearing reaction circumstances and yet give no adverse effect to the reaction system, can be mentioned. Examples of these include cellulose-based resin such as carboxymethylcellulose and hydroxyethylcellulose, fluorine-containing resin such as polyethylene tetrafluoride and polyvinylidene fluoride, polymer compounds such as urethane resin, epoxy resin, polyester resin, phenol resin, melamine resin, silicone resin, polyvinyl alcohol, polyimide resin and polyimideamide resin, and sol of such inorganic compounds as silica and alumina.

Although the internal structure of the film type catalyst depends largely on the type of active material constituting the catalyst body, the method for manufacturing the catalyst body etc., it may form a dense continuous phase or be porous. For example, a thin film formed on the surface of a support by a spattering method, chemical evaporation method etc. can have a dense continuous phase, and one formed on a support by such method as a wet or dry coating using a powdery active material may be porous.

In the present invention, the reaction between alcohol and primary or secondary amine is carried out by using a reactor loaded with the film type catalyst as described above, and controlling the superficial velocity of the liquid in the reactor. The superficial velocity of the liquid in the reactor is 0.1 cm/s or more, preferably 0.2 cm/s or more, more preferably 0.3 cm/s or more from the viewpoint of suppressing a side reaction. The upper limit of the superficial velocity of the liquid is preferably 300 cm/s, more preferably 100 cm/s, further preferably 50 cm/s from the viewpoint of reducing energy necessary for feeding the liquid to the reactor, and reducing pressure loss within the reactor generated due to the flow of the liquid.

The superficial velocity of the liquid in the reactor can be gotten from the formula (1) below using the cross-sectional area A ($cm^2$) of the reactor and the flow volume Q ($cm^3/s$) of the fed liquid.

$$\text{Superficial velocity (cm/s) of Liquid} = Q/A \quad (1)$$

As a method for controlling the superficial velocity of the liquid in the reactor loaded with the film type catalyst, various methods can be adopted including conventionally publicly known ones such as a pump, agitating blade and ejector.

The reactor loaded with the film type catalyst is operated so that the reacting substances and/or a mixture of the reaction products is fed continuously or intermittently from the outside, and that the product resulted from the reaction in the inside is discharged continuously and/or intermittently from it. As the system thereof, various ones can be adopted including conventionally publicly known ones. For example, the film type catalyst may be loaded inside a tube-reactor after being rolled as a cylinder or processed into strips. The film type catalyst also may be loaded in a tube or shell portion of a shell & tube heat exchanger type. In this instance, the temperature of the reaction portion can be controlled by flowing a heat medium on the tube side or shell side onto which no film type catalyst has been loaded. In the case of a flow system tube-reactor, it is possible to allow the reaction to proceed in a continuous system by using such system that the reacting substances are fed to the film type catalyst within the tube and, at the same time, the reaction product is collected continuously to achieve circular feeding. A system may also be adopted, in which a reactor loaded with the film type catalyst is disposed in an agitating tank and the liquid and gas are fed to the reactor and circulated by using an agitating blade.

Further, a reactor loaded with the film type catalyst may be disposed in an outside circular line ancillary to a buffering tank loaded with no catalyst to effect circulation of the liquid and/or gas between the buffering tank and the reactor, or feed the liquid continuously to several reactors.

Here, the buffering tank means a vessel for storing the raw materials necessary for the reaction and/or the reaction product generated by the reaction, and it is also possible, according to need, to separate the reaction product and/or unreacted raw materials discharged from the reactor to effect gas/liquid separation into a gas component and liquid component in the buffering tank and extract the gas component to the outside of the system. There is no particular limitation on the buffering tank provided that it is of a commonly used type. The buffering tank may have a jacket or internal coil for heating or cooling the raw material or reacting substances. Further, it may have an agitator for making the liquid uniform, or, adversely, a structure with no agitation, the structure being provided with a partition board in the buffering tank so as to enhance extrusion flowability of the reaction liquid.

The internal temperature of the reactor having been loaded with the film type catalyst may be controlled by heating from the outside of the reactor, or the inside of the reactor may be controlled at an intended temperature side previously heating the liquid and/or gas to be fed to the reactor. When it is difficult to practice the heating from the outside of the reactor, the temperature control according to the latter method is preferred.

One example of the reaction apparatus for use in the present invention is shown in FIG. 1. FIG. 1 is an example of a circulation fixed-bed type reaction apparatus, wherein 1 is a tube-reactor loaded with the film type catalyst, 2 is a buffering tank, 3 is a pump for external circulation, 4 is a conduit pipe for external circulation, 5 is a conduit pipe for a packed column, and 6 is a packed column.

The tube-reactor 1 is a perpendicular round tube type fixed-bed reactor, onto the inside of which is loaded with the film type catalyst, whose temperature can be controlled by heating from the outside. The buffering tank 2 is a storage tank of the liquid reacting substances and/or a mixture of the reaction products, which are circulated side pump 3 between the buffering tank and the reactor 1 while controlling the superficial velocity of the liquid within the reactor. Through the conduit pipe 4, the reacting substances and/or a mixture of the reaction products, and gaseous primary or secondary amine and hydrogen gas are fed continuously from the lower end of the reactor 1, and the unreacted substance and/or a mixture of reaction products and hydrogen gas are collected continuously from the upper end, which are introduced into the buffering tank 2. Through the conduit pipe 5, unreacted gaseous primary or secondary amine and moisture are discharged continuously. In the components discharged from the conduit pipe 5, in addition to those described above, vapor or mist-like components of alcohol and/or generated tertiary amine etc. are sometimes included, which are condensed and liquidized in the packed tower 6 and returned to the buffering tank 2, and remaining gas component is discharged to the outside of the system. The inside of the reaction system is maintained at around ordinary pressure.

Figure 2:
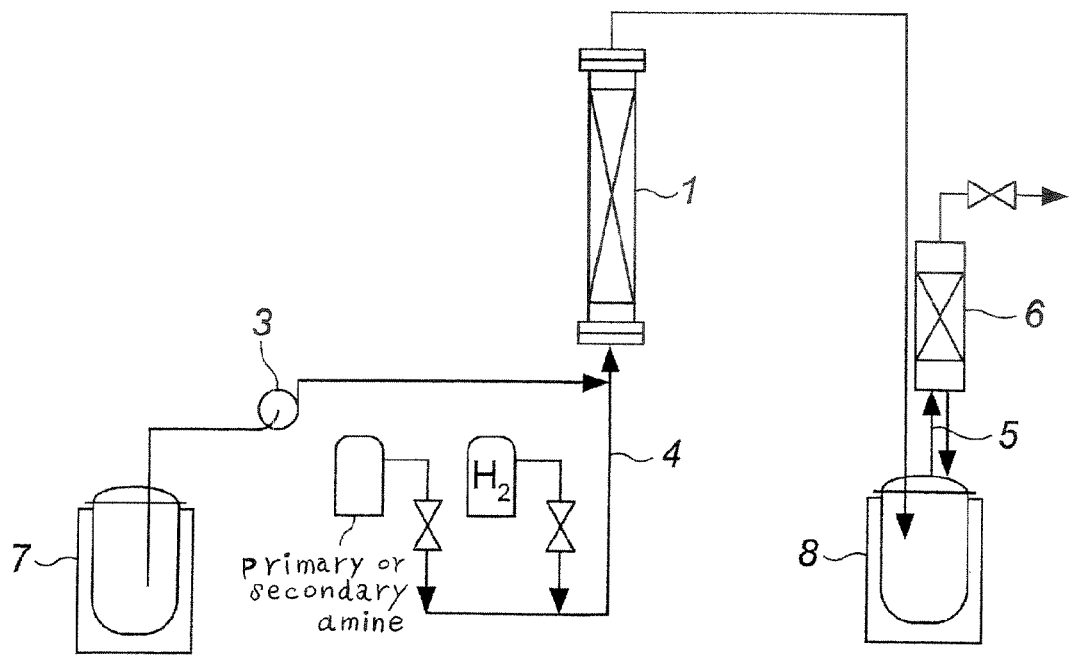
FIG. 2 shows a summary drawing showing one example of a single flow fixed-bed type reaction apparatus for use in the present invention. In the drawing, numeral References are: 1: A tube-reactor loaded with a film type catalyst, 2: Buffering tank, 3: Liquid feeding pump, 4: Conduit pipe for feeding, 5: Conduit pipe for packed tower, 6: Packed tower, 7: Raw material tank, 8: Product tank.

Another example of the reaction apparatus for use in the present invention is shown in FIG. 2. FIG. 2 shows an example of a single flow fixed-bed type reaction apparatus, wherein 1 is a tube-reactor loaded with the film type catalyst, 3 is a pump for feeding liquid, 4 is a conduit pipe for feeding, 5 is a conduit pipe for a packed tower, 6 is a packed tower, 7 is a raw material tank and 8 is a product tank.

The tube-reactor 1 is a perpendicular round tubular fixed-bed reactor, onto the inside of which is loaded with the film type catalyst, whose temperature can be controlled by heating from the outside. The raw material tank 7 is a storage tank for liquid stock alcohol and/or reacting substance, from which it is fed to the reactor 1 by the pump 3 while controlling the superficial velocity of the liquid within the reactor. Through the conduit pipe 4, the stock alcohol and/or the reacting substance, and gaseous primary or secondary amine and hydrogen gas are fed continuously from the lower end of the reactor 1, and, from the upper end, unreacted substance and/or a mixture of the reaction products and hydrogen gas are collected continuously to be introduced into the product tank 8. Unreacted gaseous primary or secondary amine and moisture are discharged continuously through the conduit pipe 5. In the components discharged from the conduit pipe 5, in addition to those described above, vapor or mist-like components of alcohol and/or generated tertiary amine etc. are sometimes included, which are condensed and liquidized in the packed tower 6 and returned to the product tank 8, and remaining gas component is discharged to the outside of the system. The inside of the reaction system is maintained at around ordinary pressure.

The reaction conditions of an alcohol with a primary or secondary amine in the present invention differ depending on the reacting substances, reaction products and type of the catalyst. The reacting substances may exist in a gas phase or liquid phase. When a gas phase exists in the reaction system, it is preferred to allow them to react with each other under a hydrogen, nitrogen and/or rare gas atmosphere in point of maintaining the activity of the catalyst. In a two-phase reaction system of gas/liquid, when each of alcohol and primary or secondary amine exists in different phases, it is preferred to accelerate material transfer between the two phases by gas bubbling etc. into the liquid. For example, there are such methods as injecting the gas from a single tube into the liquid, injecting the gas from a multitube nozzle or a straight or bent tube-shaped multihole nozzle, and passing the liquid and gas through a static mixer. In addition, there can be mentioned such method as spraying the liquid into the gas-feeding flow. It is also possible to obtain the material transfer-accelerating effect by feeding the reacting substances in a gas/liquid mixed phase into a reaction field in which thin flow passages having a diameter of around several millimeters or less have been formed by the film type catalyst.

The pressure in the system is preferably not remarkably increased beyond ordinary pressure. The reaction temperature differs according to the type of the catalyst, and reacting them at a temperature of 150-300° C. is preferred By discharging side produced moisture to the outside of the reaction system, it is possible to accelerate the progress of the reaction and maintain the activity of the catalyst.

According to the present invention, it becomes possible to obtain the targeted tertiary amine in high yield while using alcohol and primary or secondary amine as raw materials by a simple process that requires no separation operation of the catalyst.

EXAMPLES

The present invention is described in more detail by reference to the Examples below. The Examples are mere illustrative of the present invention and are not intended to limit the present invention.

In Examples below, "%" and "part" indicate "% by mass" and "part by mass," respectively, unless otherwise noted.

Manufacture Example 1

Manufacture of Film Type Catalyst A

A film type catalyst A, in which a powdery catalyst was fixed using phenol resin as a binder, was prepared as follows.

In a flask having a volume of one litter, synthetic zeolite was charged, and then a solution prepared by dissolving copper nitrate, nickel nitrate and ruthenium chloride in water so as to give Cu:Ni:Ru=4:1:0.01 in mol ratio of respective metal atoms was put, whose temperature was raised with stirring. At 90° C., an aqueous 10% sodium carbonate solution was gradually dropped while controlling the pH at 9-10. After 1-hour aging, the precipitation was filtered and washed with water, and then dried at 80° C. for 10 hours, which was burned at 600° C. for 3 hours to give a powdery catalyst. The obtained powdery catalyst contained the metal oxides at a ratio of 50%, and the synthetic zeolite at a ratio of 50%.

To 100 parts of the powdery catalyst described above, phenol resin (PR-9480, manufactured by SUMITOMO BAKELITE Co., Ltd., nonvolatile content: 58%) was added as a binder so as to give the nonvolatile content of the resin of 47.7 parts. Further, 2-butanone was added as a solvent so as to give a ratio of solid content (powdery catalyst and nonvolatile content of phenol resin) of 55%. It was premixed for 10 minutes using a dispersing apparatus, and then subjected to mixing and dispersing treatment using a basket mill (SS-3, manufactured by ASADA IRON WORKS CO., LTD., charged with 800 mL, 1900 g of titania beads having the diameter of 1.4 mm) at 1500 rpm for 70 minutes to manufacture paint. On both surfaces of copper foil (thickness: 40 µm, 6.5 cm×410 cm×1 sheet) as a support, the paint was coated with a bar coater and dried at 150° C. for 30 seconds. One half of the dried product was bent into a corrugated plate and superimposed on the remaining other half being a flat plate. The resultant was rolled and then subjected to hardening treatment at 150° C. for 90 minutes to fix the film type catalyst on the both surfaces of the copper foil. The obtained film type catalyst had a thickness of 4.9 µm per one surface excluding the copper foil.

Manufacture Example 2

Manufacture of Film Type Catalyst B

A film type catalyst B in which a powdery catalyst was fixed using phenol resin as a binder, was prepared as follows.

To 100 parts of the powdery catalyst manufactured according to Manufacture Example 1, phenol resin (PR-9480, manufactured by SUMITOMO BAKELITE Co., Ltd., nonvolatile content: 58%) was added as a binder so as to give the nonvolatile content of the resin of 47.7 parts. Further, 4-methyl-2-pentanone was added as a solvent so as to give a ratio of solid content (powdery catalyst and nonvolatile content of phenol resin) of 55%. It was premixed for 10 minutes using a dispersing apparatus, and then subjected to mixing and dispersing treatment using a basket mill (SS-3, manufactured by ASADA IRON WORKS CO., LTD., charged with 800 mL, 1900 g of titania beads having the diameter of 1.4 mm) at 1500 rpm for 70 minutes to manufacture paint. On both surfaces of copper foil (thickness: 40 µm, 0.3 m×36 m) as a support, the paint was coated with a gravure bar coater and dried at 150° C. for 30 seconds. The dried product was cut into 27 cm×429 cm×16 sheets, one half of which were bent into a corrugated plate and superimposed alternately on the remaining tabular products being a flat plate. The resulting product was loaded onto a cylindrical holder for use in the perpendicular round tubular fixed-bed reactor 1 shown in FIG. 1, and then subjected to hardening treatment at 150° C. for 90 minutes to fix the film type catalyst onto the both surfaces of the copper foil. The obtained film type catalyst had a thickness of 5.4 µm per one surface excluding the copper foil.

In Examples 1 and 2, and Comparative Example 1 below, N-dodecyl-N,N-dimethylamine (hereinafter, it is described as "DM type") was manufactured from lauryl alcohol and dimethylamine as raw materials using the single flow fixed-bed type reaction apparatus shown in FIG. 2. In Examples 3 and 4, the DM type was manufactured from lauryl alcohol and dimethylamine as raw materials using the circular fixed-bed type reaction apparatus shown in FIG. 1.

Example 1

The film type catalyst A obtained in Manufacture Example 1 was loaded on to the inside of the tube-reactor 1 having an inner diameter of 29.5 mm. The loaded portion of the film type catalyst had a length of 390 mm, and a volume of 0.267 L to form plural flow paths having a cross-sectional area of around 0.1 cm$^2$ that communicated in the axial direction of the reactor 1 by the film type catalyst. 1.0 kg of lauryl alcohol (Kalcol 20, manufactured by KAO CORPORATION) was charged in the raw material tank 7 and, while feeding hydrogen gas in a flow volume of 20 L/Hr in terms of the volume in the standard state, the liquid superficial velocity of the tube-reactor 1 was set at 0.30 cm/s.

The raw material was fed continuously from the raw material tank 7 to the reactor 1 and, after raising the inside temperature of the reactor 1 up to 220° C., the reaction was begun by feeding dimethylamine. The unreacted raw materials and a mixture of the reaction products flowing continuously from the outlet of the reactor 1 were collected into the product tank 8. A cycle was repeated, in which the mixture collected into the product tank 8 was fed again continuously from the raw material tank 7 to reactor 1 by the similar operation and those subjected to the reaction in the reactor were collected into the product tank 8.

After 3 hours from the beginning of the reaction, the feed of the dimethylamine was stopped, and the whole volume of the liquid within the product tank 8 and reactor 1 was drawn. The liquid was analyzed with gas chromatograph. The result of quantification by the area percentage method gave 12.3% of unreacted lauryl alcohol, 82.3% of generated DM type, and 3.8% of M2 type being side produced tertiary amine. N,N,N-tridodecylamine was not detected.

Example 2

The internal temperature of the reactor 1 was raised up to 220° C. in the same operation as in Example 1 except for setting the liquid superficial velocity of the tube-reactor at 0.20 cm/s, and then the reaction was begun by feeding dimethylamine. The feed volume of the dimethylamine was adjusted in accordance with the progress of the reaction, and 86 g/Hr in the reaction time average.

After 3 hours from the beginning of the reaction, the feed of the dimethylamine was stopped, and the whole volume of the liquid within the product tank 8 and reactor 1 was drawn. The liquid was analyzed with gas chromatograph as was the case with Example 1. The result gave 12.6% of unreacted lauryl alcohol, 80.1% of generated DM type, and 5.0% of M2 type being side produced tertiary amine.

Example 3

The film type catalyst B obtained in Manufacture Example 2 was loaded onto the inside of the reactor 1 having an inner diameter of 101 mm. The loaded portion of the film type catalyst had a length of 2160 mm, and a volume of 17.4 L to form plural flow paths having a cross-sectional area of around 0.1 cm$^2$ that communicated in the axial direction of the reactor 1 by the film type catalyst. 46.1 kg of lauryl alcohol (Kalcol 20, manufactured by KAO CORPORATION) was charged in the buffering tank 2 and, while feeding hydrogen gas in a flow volume of 922 L/Hr in terms of the volume in the standard state, the liquid was circulated between the buffering tank 2 and reactor 1, and the liquid superficial velocity of the tube-reactor 1 was set at 2.40 cm/s. After raising the temperature within the reactor 1 up to 220° C., the reaction was begun by feeding dimethylamine at 220° C. The feed volume of the dimethylamine was adjusted in accordance with the progress of the reaction. After 1 hour from the beginning of the reaction, the feed of the dimethylamine was stopped, and the whole volume of the liquid within the buffering tank 2 and reactor 1 was drawn. The liquid was analyzed with gas chromatograph. The result of quantification by the area percentage method gave 15.3% of unreacted lauryl alcohol, 78.6% of generated DM type, and 3.7% of M2 type being side produced tertiary amine. N,N,N-tridodecylamine was not detected.

Example 4

The internal temperature of the reactor 1 was raised up to 220° C. in the same operation as in Example 3 except for setting the liquid superficial velocity of the reactor 1 at 0.80 cm/s, and then the reaction was begun by feeding dimethylamine. The feed volume of the dimethylamine was adjusted in accordance with the progress of the reaction. After 1 hour from the beginning of the reaction, the feed of the dimethylamine was stopped, and the whole volume of the liquid within the buffering tank 2 and reactor 1 was drawn. The liquid was analyzed with gas chromatograph in the same way as in Example 3. The result gave 13.9% of unreacted lauryl alcohol, 80.2% of generated DM type, and 4.4% of M2 type being side produced tertiary amine.

Comparative Example 1

The film type catalyst A obtained in Manufacture Example 1 was loaded onto the inside of the tube-reactor 1 having an inner diameter of 28.5 mm. The loaded portion of the film type catalyst had a length of 800 mm, and a volume of 0.510 L to form plural flow paths having a cross-sectional area of around 0.1 cm$^2$ that communicated in the axial direction of the reactor 1 by the film type catalyst. The internal temperature of the reactor 1 was raised up to 220° C. in the same operation as in Example 1 except for setting the liquid superficial velocity of the reactor 1 at 0.01 cm/s, and then the reaction was begun by feeding dimethylamine at 220° C. The feed volume of the dimethylamine was set at a constant value of 66 g/Hr. The liquid reacted and sent to the product tank 8 was drawn every 1 hour. The drawn liquid was analyzed with gas chromatograph. The result of quantification by the area percentage method (result of one-pass analysis) gave 14.5% of unreacted lauryl alcohol, 73.2% of generated DM type, and 10.3% of M2 type being side produced tertiary amine. N,N,N-tridodecylamine was not detected.

The results of Examples 1-4 and Comparative Example 1 are shown collectively in Table 1.

TABLE 1

|  |  |  | Example | | | | Comparative example |
|---|---|---|---|---|---|---|---|
|  |  |  | 1 | 2 | 3 | 4 | 1 |
| Film-type catalyst | Kind | | Catalyst A | | Catalyst B | | Catalyst A |
|  | Thickness*1 | (μm) | 4.9 | | 5.4 | | 4.9 |
|  | catalyst volume*2 | (g-film-type catalyst) | 5.0 | | 384 | | 8.3 |
|  | Film area | (m²-Film) | 0.53 | | 37 | | 1.03 |
| Tube-reactor | Diameter of reactor | (mm) | 29.5 | 29.5 | 101 | 101 | 28.5 |
|  | Volume of loaded portion of catalyst | (L) | 0.267 | 0.267 | 17.4 | 17.4 | 0.51 |
| Reaction conditions | Starting material alcohol | (kg) | 1.0 | 1.0 | 46.1 | 46.1 | 1.0 |
|  | Liquid flow volume | (L/Hr) | 7.5 | 5.0 | 692 | 231 | 0.32 |
|  | Liquid superficial velocity | (cm/s) | 0.30 | 0.20 | 2.40 | 0.80 | 0.01 |
|  | Reaction tower temperature | (° C.) | 220 | 220 | 220 | 220 | 220 |
|  | Hydrogen flow volume | (NL/Hr) | 20 | 20 | 922 | 922 | 20 |
|  | Dimethylamine flow volume (average reaction time) | (g/Hr) | 79 | 86 | 3500 | 3500 | 66 |
|  | Reaction time | (Hr) | 3.0 | 3.0 | 1.0 | 1.0 | 1.6 |
| Reaction results | Lauryl alcohol | (%) | 12.3 | 12.6 | 15.3 | 13.9 | 14.5 |
|  | M2 Type*3 | (%) | 3.8 | 5.0 | 3.7 | 4.4 | 10.3 |
|  | DM Type*4 | (%) | 82.3 | 80.1 | 78.6 | 80.2 | 73.2 |

Note)
*1 The thickness of the catalyst layer excluding copper foil
*2 The film catalyst volume excluding copper foil
*3 N,N-didodecyl-N-methylamine
*4 N-dodecyl-N,N-dimethylamine

The invention claimed is:

1. A method for manufacturing a tertiary amine, comprising the step of reacting a tertiary amine with an alcohol and a primary or secondary amine in a reactor loaded with a film type catalyst, controlling the superficial velocity of the reactor at 0.1 cm/s or more.

2. The method for manufacturing a tertiary amine according to claim 1, wherein the reaction is carried out by disposing the reactor in an outside circular line ancillary to a buffering tank loaded with no catalyst and circulating the reacting liquid to the reactor.

3. The method for manufacturing a tertiary amine according to claim 1 or 2, wherein the film type catalyst is fixed on the surface of a support and the thickness of the catalyst is 0.01-500 μm.

4. The method for manufacturing a tertiary amine according to claim 1 or 2, wherein the alcohol is a linear or branched, saturated or unsaturated aliphatic alcohol having 8-36 carbon atoms.

5. The method for manufacturing a tertiary amine according to claim 1 or 2, wherein the primary or secondary amine is an aliphatic primary or secondary amine.

* * * * *